United States Patent [19]

Danon

[11] Patent Number: 5,049,147
[45] Date of Patent: Sep. 17, 1991

[54] APPARATUS FOR COMPUTERIZED LASER SURGERY

[76] Inventor: Nissim N. Danon, Flat 29, 15 Rabina St., Ramat Aviv, Israel

[21] Appl. No.: 493,108

[22] Filed: Mar. 13, 1990

[30] Foreign Application Priority Data

Apr. 6, 1989 [IL] Israel .................................. 89874

[51] Int. Cl.⁵ .............................................. A61B 17/36
[52] U.S. Cl. .......................................... 606/10; 606/4; 606/11; 364/413.13; 128/395
[58] Field of Search ...................... 606/2, 7, 8, 10–16, 606/4–6; 604/20, 21; 128/633, 634, 653 R, 395–398; 364/413.20–413.22, 413.13; 219/121.61, 121.62

[56] References Cited

U.S. PATENT DOCUMENTS

| | | | |
|---|---|---|---|
| 4,454,882 | 6/1984 | Takano | 128/395 |
| 4,503,854 | 3/1985 | Jako . | |
| 4,538,608 | 9/1985 | L'Esperance, Jr. . | |
| 4,597,649 | 7/1986 | Swaniger et al. . | |
| 4,598,368 | 7/1986 | Umemura | 364/413.22 |
| 4,638,800 | 1/1987 | Michel | 606/14 |
| 4,665,913 | 5/1987 | L'Esperance, Jr. . | |
| 4,669,466 | 6/1987 | L'Esperance . | |
| 4,672,963 | 6/1985 | Barken | 606/12 |
| 4,686,992 | 8/1987 | Dewey et al. . | |
| 4,718,418 | 1/1988 | L'Esperance, Jr. . | |
| 4,722,056 | 1/1988 | Roberts et al. | 364/413.22 |
| 4,729,372 | 3/1988 | L'Esperance, Jr. . | |
| 4,791,934 | 8/1986 | Brunnett . | |
| 4,887,605 | 12/1989 | Angelson et al. | 128/395 |

FOREIGN PATENT DOCUMENTS 0071185 7/1982 European Pat. Off. .
8500010 6/1984 World Int. Prop. O. .

OTHER PUBLICATIONS

Electronique Applications, No. 58, Feb–Mar. 1988, pp. 67–70 (french).
Jean et al., "Eye Tracking for Image Stabilization", in Lasers in Ophthalmology, vol. 1, No. 4, pp. 197–204 (1987).

Primary Examiner—Stephen C. Pellegrino
Assistant Examiner—Steven J. Shumaker
Attorney, Agent, or Firm—Darby & Darby

[57] ABSTRACT

There is provided an apparatus and methods for computerized laser surgery. The apparatus comprises apparatus for displaying in real time a visually sensible image of the area of surgery, apparatus for displaying in overlap over the visually sensible image a simulation of the effects of operator indicated laser surgical procedures on the area of surgery and automated apparatus for carrying out the operator indicated laser surgical procedures following the display thereof. The method includes the steps of simulating the effects of operator indicated laser surgical procedures on an area of surgery, tuning parameters of a beam of a surgical laser, aiming the apparatus for transmitting laser energy at each point of the surgery, low energy firing of the low energy laser beam at an operator indicated surgery point thereby to ensure that the surgical laser is correctly aimed and high energy firing of the surgical laser at the operator indicated surgery point thereby to treat the point.

19 Claims, 8 Drawing Sheets

SH. 1 OF 2

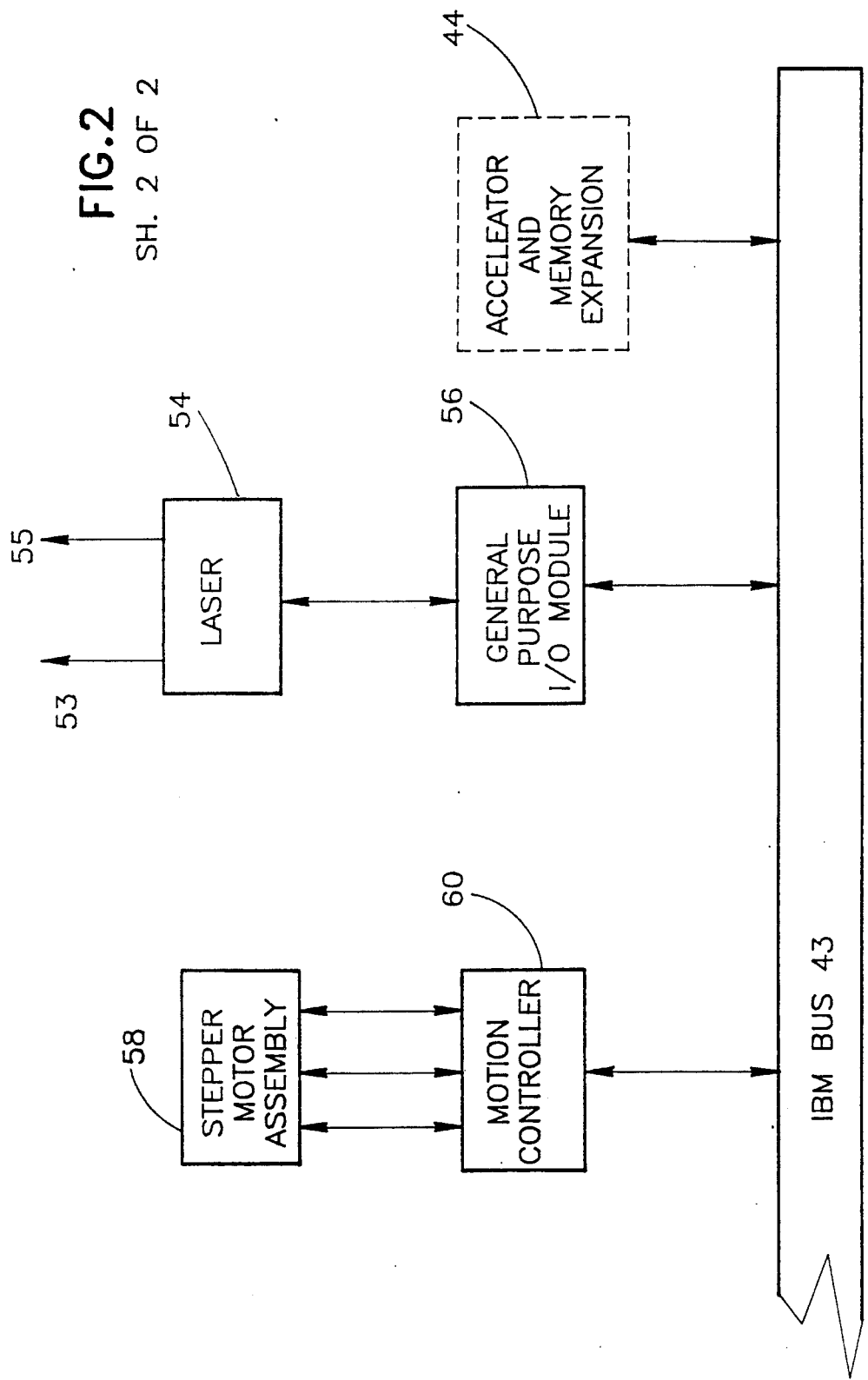

SH.1 OF 4

SH. 2 OF 4

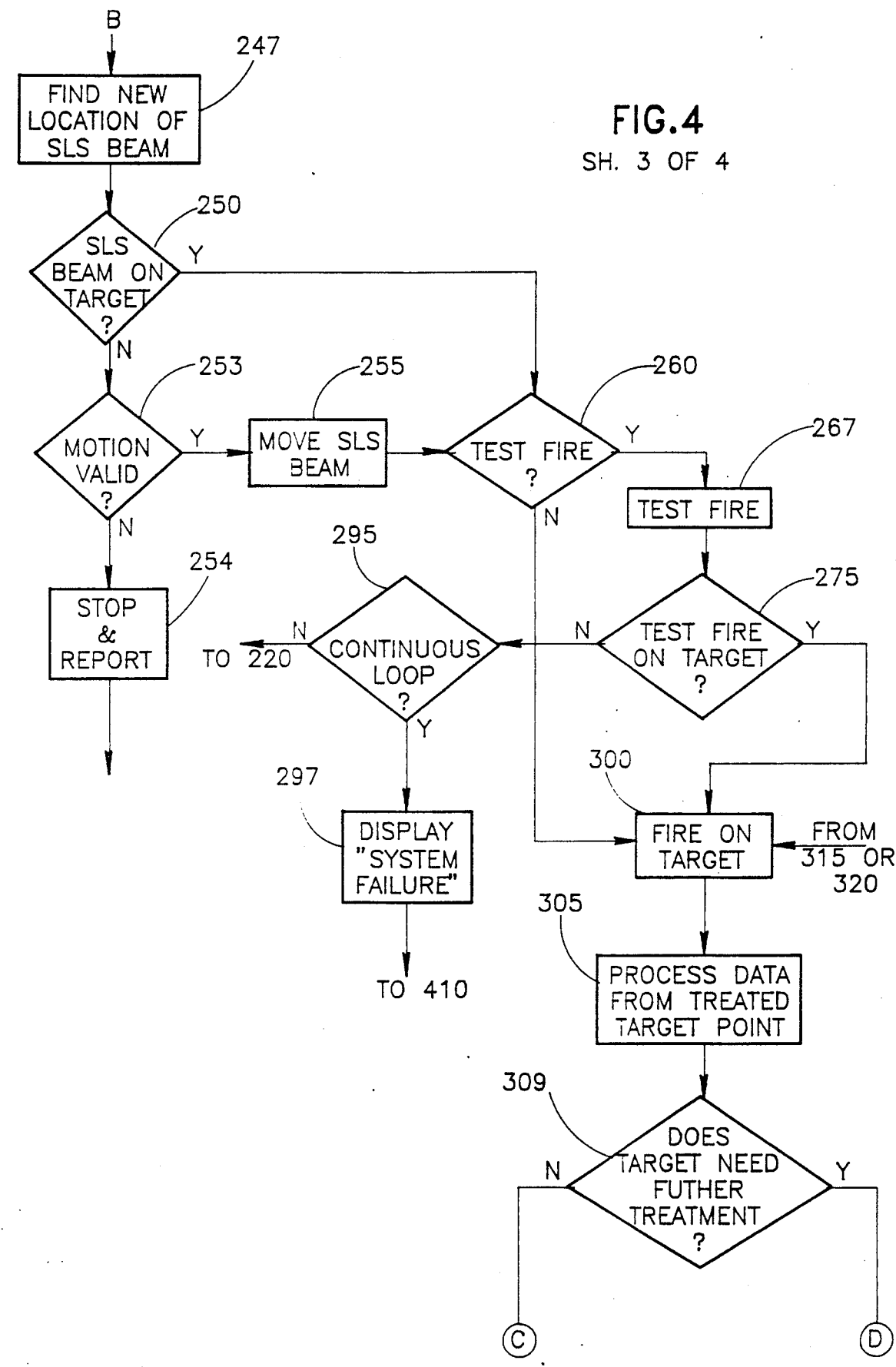
FIG.4 SH. 3 OF 4

SH. 4 OF 4

APPARATUS FOR COMPUTERIZED LASER SURGERY

FIELD OF THE INVENTION

The present invention relates to laser surgery generally and has particular applicability to ophthalmic laser surgery.

BACKGROUND OF THE INVENTION

Almost since their invention, lasers have been successfully utilized for delicate surgery, such as ophthalmic surgery. Delicate surgery, by its nature, requires precise placement of the cut, or burn of the laser, in order to avoid irreparable damage to the tissue under treatment. Lasers aim only a small beam of light at the tissue, but the accuracy of the aim depends on the surgeon's skill and the lack of movement on the part of the area to be treated. Various apparatus and techniques for laser surgery exist and are described in the patent literature:

U.S. Pat. No. 4,597,649 describes information display apparatus for ophthalmic slit lamps wherein an LED display is provided between the collimator and the eyepiece and is suitable for display of laser operational data in addition to positional data.

U.S. Pat. No. 4,503,854 describes ceiling mounted laser surgery apparatus having a motorized micromanipulator delivery system which is compatible with a microprocessor for automated surgery. A built in digital television system is provided for demonstration, recording or for use as a robotic eye in association with a computer used to control the laser surgery.

U.S. Pat. No. 4,638,800 describes a laser beam surgical system including a cannula which carries a white light conduit and a carbon dioxide laser light conduit.

U.S. Pat. No. 4,686,992 describes an ophthalmic beam director having an automatic centering device.

U.S. Pat. No. 4,722,056 describes reference display systems for superimposing a tomographic image onto the focal plane of an operating microscope.

U.S. Pat. Nos. 4,538,608; 4,669,466; 4,665,913; 4,718,418 and 4,729,372 all to L'Esperance, Jr. all relate to laser ophthalmological surgery.

U.S. Pat. No. 4,672,963 describes an apparatus and method for computer controlled laser surgery. The computer system provides a display of tissue, acquired with ultrasonic means, within the patient. The attending physician provides input, describing tissue to be irradiated, with a light pen into the computer. The computer system then controls both the duration and intensity of the laser burst to accomplish tissue destruction. The system is not fully automated and depends on input from the attending physician, during the surgical operation, to define the areas to be irradiated and to position the laser guide. In addition, the system depends on ultrasonic means for its image acquisition.

B. Jean, et al, in a paper, "Eye Tracking for Image Stabilization," in Lasers in Ophthalmology, discuss a system for real-time tracking of eye movements and image stabilization. The system effectively tracks eye structures on the retina and in the anterior eye; however, it is not operative to perform surgery. The system described in the paper does not incorporate the processes of firing a laser beam at a target point, checking that the burn was properly placed and moving to the next target point which are necessary for an automatic laser surgical system.

SUMMARY OF THE INVENTION

The present invention seeks to provide real time computerized surgery apparatus suitable for use in laser surgery.

There is thus provided in accordance with the preferred embodiments of the present invention apparatus for computerized laser surgery including apparatus for displaying in real time a visually sensible image of the area of surgery, apparatus for displaying in overlay over the visually sensible image a simulation of the effects of operator indicated laser surgical procedures on the area of surgery and automated apparatus for carrying out the operator indicated laser surgical procedures following the display thereof.

Further in accordance with the preferred embodiments of the invention the apparatus for displaying in real time a visually sensible image of the area of surgery includes apparatus for image acquisition, preferably, employing an electro-magnetic radiation sensor, such as one responsive to visible light. Alternate embodiments of the apparatus for image acquisition may use ultraviolet light, infrared light, x-rays, gamma-rays or nuclear magnetic resonance (NMR) imaging or a suitable combination thereof. A further embodiment of the apparatus for image acquisition incorporates computerized tomography and a still further embodiment incorporates catheter-based imaging systems.

Further in accordance with the preferred embodiments of the invention the apparatus for displaying in overlay includes apparatus for transmitting low energy laser energy (i.e. a He-Ne laser) over substantially the same optical path to be subsequently traveled by higher energy laser energy producing the operator indicated laser surgical procedures. It will be appreciated that the terms "higher energy laser" and "high energy laser" as utilized herein refer to a surgical laser. The terms are utilized to differentiate the higher power surgical laser from the lower energy laser also incorporated into the present invention.

Additionally in accordance with the preferred embodiments of the invention there is provided apparatus for input of operator instructions for setting the parameters of the operator indicated laser surgical procedures. Preferably this apparatus employs a light pen which is interactively employed with the apparatus for displaying. An alternative embodiment employs a mouse or a cursor.

Additionally in accordance with the preferred embodiments of the present invention, the automated apparatus for carrying out the operator indicated laser surgical procedures includes apparatus for tracking the effects of surgical procedures already carried out and comparing them in real time with the operator indications therefor.

Further in accordance with the preferred embodiments of the invention, the automated apparatus also includes apparatus for applying predetermined criteria to the effects of surgical procedures already carried out.

There is additionally provided in accordance with a preferred embodiment of the invention, a method for computerized surgery including the steps of simulating the effects of operator indicated laser surgical procedures on an area of surgery, automatically tuning parameters of a beam of a surgical laser, automatically aiming the surgical laser beam at each point of the surgery site, low energy firing of the He-Ne laser at an operator indicated surgery point thereby to ensure that the surgical laser is correctly aimed and high energy firing of the surgical laser at the operator indicated surgery point thereby to treat the point.

Additionally, according to a preferred embodiment of the invention, the method includes the steps of tracking the effects of surgical procedures already carried out and of comparing in real time the effects of surgical procedures already carried out with the operator indications therefor. The method preferably applies predetermined criteria to the effects of surgical procedures already carried out. The method additionally includes a step of inputting operator instructions for setting parameters of the operator indicated surgery.

Further, according to a preferred embodiment of the invention, certain operations that are automatically performed may be performed manually. Such operations include the aiming of the surgical beam and the tuning of the beam parameters.

Still further, according to a preferred embodiment of the invention, the step of automatic aiming includes the steps of acquiring an image, identifying the locations of reference points in the image previously defined in the step of inputting, identifying the location of a target point from the reference points and moving the surgical laser beam thereby to aim at the target point. Preferably, the reference points are features in the image. It will be appreciated that the term "target point" refers generally to the next location to be burned rather than to a location specifically defined by the operator.

BRIEF DESCRIPTION OF THE DRAWINGS

The present invention will be more fully understood and appreciated from the following detailed description, taken in conjunction with the drawings in which.

DETAILED DESCRIPTION OF A PREFERRED EMBODIMENT

The preferred embodiment of the computerized laser surgical system of the present invention involves ophthalmological surgery. However, it will be appreciated by those skilled in the art that the system of the invention is not limited to opthamological surgery.

Figure 1:
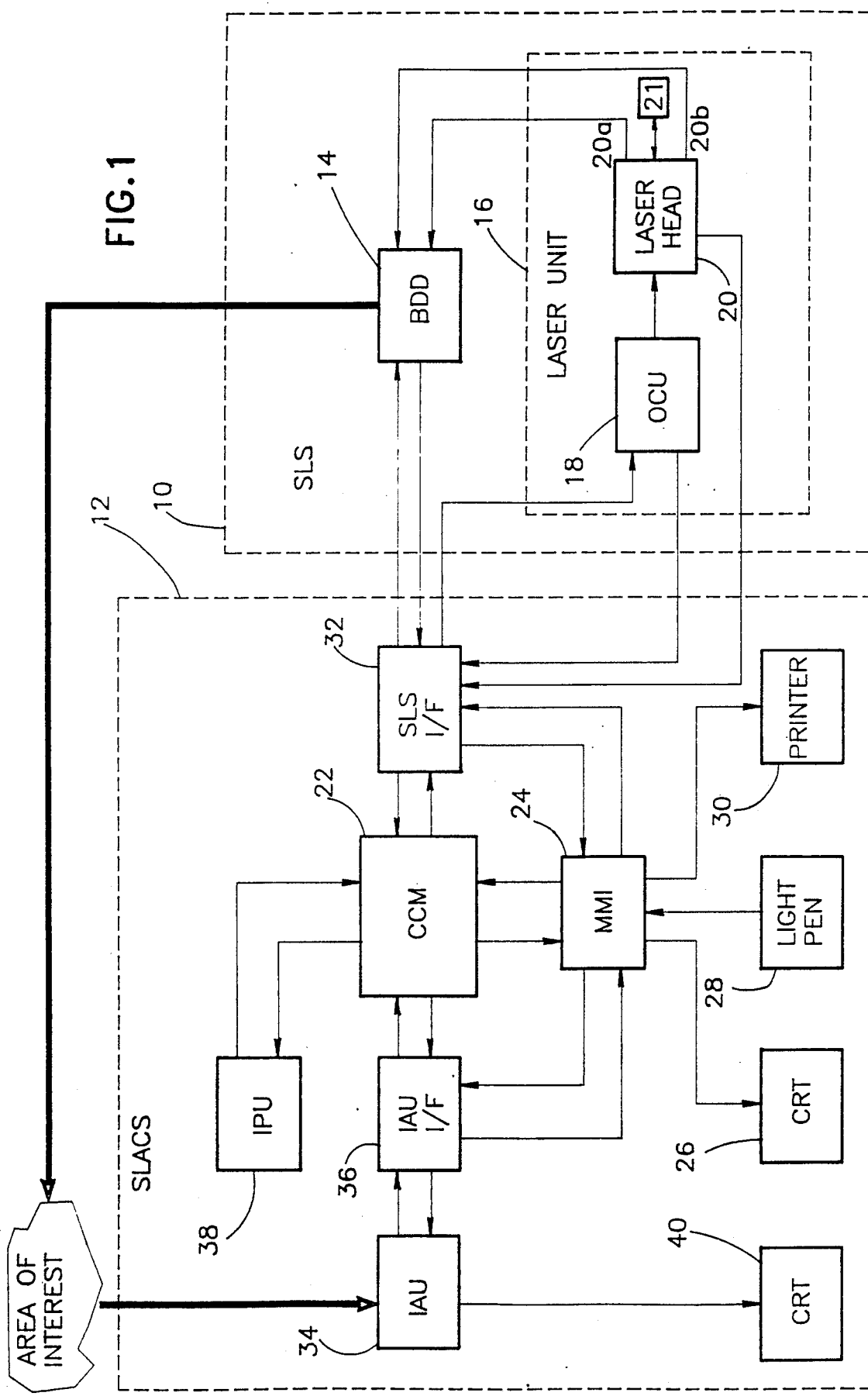
FIG. 1 is a functional block diagram illustration of a computer controlled laser surgery system.

Reference is now made to FIG. 1, which functionally illustrates a computer controlled laser surgery system. The system comprises two main subsystems, a SLS (Surgical Laser Subsystem) 10 and a SLACS (Surgical Laser Actuator and Control Subsystem) 12.

The SLS subsystem 10 may comprise any suitable commercially available surgical laser system. It typically comprises one or more BDD (Beam Delivery Devices) 14, and a laser unit 16, which includes an OCU (Operation Control Unit) 18, at least one laser head 20, typically comprising both a He-Ne low energy aiming head 20a, useful for aiming a surgical laser beam, and an Ar surgical laser 20b, and a sensor unit 21.

The SLACS subsystem 12 typically comprises a CCM (Central Computing and data Management) unit 22 which is responsible for overall data and system management of the entire laser surgery system. The software running the CCM 22 typically includes modules for defining the system-wide variables and priorities for the various software tasks, for tracking the beam location and generating the commands controlling the operations of the SLS subsystem 10 and for diagnosing and testing the system. The software of the CCM 22 additionally provides timing and triggering outputs to the various blocks and units of the system, as will be described hereinbelow.

One software module of the CCM 22, the diagnostics and built in tests module, typically is responsible for all the automatic checks necessary to ensure that the system is operating properly. The two main groups of checks performed by this module are set-up checks, before the beam is delivered; and on-line checks, to ensure that the system is operating according to the operator's instructions.

An MMI (Man-Machine Interface) block 24 is interconnected with the CCM 22. MMI 24 provides an interface between the operator of the system and the SLACS subsystem 12, thus enabling the operator to set and introduce operation parameters and to receive feedback regarding the surgery by means of peripheral units such as a CRT display 26 useful in communicating with the user, a light pen 28, and a printer 30. It will be appreciated that light pen 28 can be implemented as a mouse or any other suitable input peripheral.

Specifically, the MMI 24 collects the operation parameters of the SLS subsystem 10 through the keyboard and/or functional keys; accepts the operator's commands for system control, particularly for imaging and beam delivery; collects light-pen information; collects on-line parameter modifications made by the operator; displays the image of the operation site, the area of interest delimited as described hereinbelow, parameter values as set by the operator, and warning and alarm announcements; produces hard copies of data for documentation; and generally collects and displays all data respectively coming into and going out of the system by means of the peripheral units.

An IAU (Image Acquisition Unit) 34 typically comprises a state of the art electronic camera and an illumination sub-unit. An IAU interface (IAU I/F) unit 36 interconnects IAU 34 to the various blocks and units of the SLACS subsystem 12, and provides an interface therebetween. IAU I/F 36 typically comprises an A/D converter and typically operates at 20 Mhz. A software module, typically resident in and controlled by the CCM 22, collects from the IAU I/F 36 information regarding the imaged area and arranges it in data structures for further processing. IAU 34 is positioned and aligned according to real time instructions transmitted by the operator via MMI 24, CCM 22 and IAU I/F 36. IAU 34 typically has five degrees of freedom of movement that enable it to be positioned and aligned for real-time tracking. The five degrees of freedom may be provided mechanically or it may be provided optically by a set of the lenses which are part of the IAU 34. In the latter embodiment, the lenses provide movement in the three translational directions and the remaining two degrees of freedom, the angular movement are provided mechanically. After positioning and alignment, IAU 34 acquires the image of the area of interest in the patient's eye, according to imaging parameters received from MMI 24 via CCM 22 and IAU I/F 36.

IAU 34 is additionally directly connected with a second CRT display unit 40 for the purpose of displaying to the surgeon the image of the area of interest.

An IPU (Image Processing Unit) 38 typically comprises the hardware necessary for the implementation of the image processing software resident in the CCM 22. The image processing software typically processes an image which has been collected by the IAU I/F module. The image is typically compared with previous images, and the differences are analyzed to evaluate the effect of the surgery. The image processing software, thus, has two main tasks, to provide the surgeon with real-time numerical and graphical analysis and feedback from the surgery site and to maintain the information about the area that has been treated.

The raw image acquired by the IAU 34 is transmitted from it to IPU 38, via IAU I/F 36. IPU 38 then processes the raw image, as described hereinabove, and then transmitted to CCM 22.

An SLS interface (SLS I/F) block 32 interconnects the SLS 10 and SLACS 12 subsystems. It receives signals representing operation parameters of the SLS subsystem 10, such as beam directioning and positioning, as set by the operator via the MMI 24. It makes any necessary corrections, and then actuates laser head 20 via OCU 18 and the BDD unit 14. Additionally, it collects real-time feedback data from the SLS subsystem 10.

All the set-up and on-line measurements concerning the beam parameters, excepting the focusing scheme, preferably are performed by the electro-optical devices installed in laser head 20 which then transmits them back to the SLACS subsystem 12 via SLS I/F 32. This ensures that the beam delivered to the area of interest is constantly checked and kept at operation conditions as set by the operator.

The SLACS subsystem 12 controls the beam pointing, beam focusing and the scanning functions of BDD 14 according to the initial parameters introduced by the operator and to the on-line real-time information transmitted by IPU 38 to CCM 22. To this end, the BDD 14 typically has five degrees of freedom of movement that enable the beam to be aimed, positioned and to scan, in three dimensions. The five degrees of freedom may be provided mechanically or it may be provided optically by a set of the lenses which are part of the BDD 14. In the latter embodiment, the lenses provide movement in the three translational directions and the remaining two degrees of freedom, the angular movement are provided mechanically.

As described hereinabove, the SLS 10 and SLACS 12 subsystems are mechanically and electronically interfaced to form one integrative system, enabling the SLACS subsystem 12 to take over complete control of the functions of the SLS subsystem 10. The SLACS subsystem 12 preferably has several modes of operation, which determine to what degree it actually controls the functions of the SLS subsystem 10. There follows a description of a typical series of such modes.

In the Automatic Mode, all the components of the system are linked substantially as described hereinabove. CCM 22 controls and inspects all operations of the system according to initial parameters and instructions introduced by the operator, and according to real-time on-line feedback from the IPU 38 and the SLS subsystem 10.

In the Semi-Automatic Mode, the interconnection between BDD 14 and SLS I/F 32 is limited to the transmittal of feedback from BDD 14 to SLS I/F 32. The directioning and positioning of BDD 14 is performed manually, preferably by the surgeon, and not by the SLACS subsystem 12. However, in this mode the SLACS subsystem 12 maintains control of the beam parameters of the SLS subsystem 10. In Semi-Automatic mode, the firing of the surgical laser head 20b is typically performed only after a test-fire of the aiming laser head 20a ensures that the manual positioning is correct.

In the Manual Mode, the interconnection of BDD 14 and OCU 18 with SLS I/F 32 is limited to the transmittal of feedback from BDD 14 and OCU 18 to SLS I/F 32. All functions and operations of the SLS subsystem 10 are controlled and performed manually, preferably by the surgeon. In this mode of operation, the SLACS subsystem 12 effectively functions as a computerized system for visual inspection and real-time feedback transmission. As in the Semi-Automatic mode, the surgeon typically fires the surgical laser head 20b only after a test-fire of the aiming laser head 20a ensures that the manual positioning is correct.

In the Diagnosis Mode, there is no interconnection at all between the SLS 10 and the SLACS 12 subsystems. In this mode, the SLACS subsystem 12 effectively functions as a simple computerized vision system.

Figure 2:
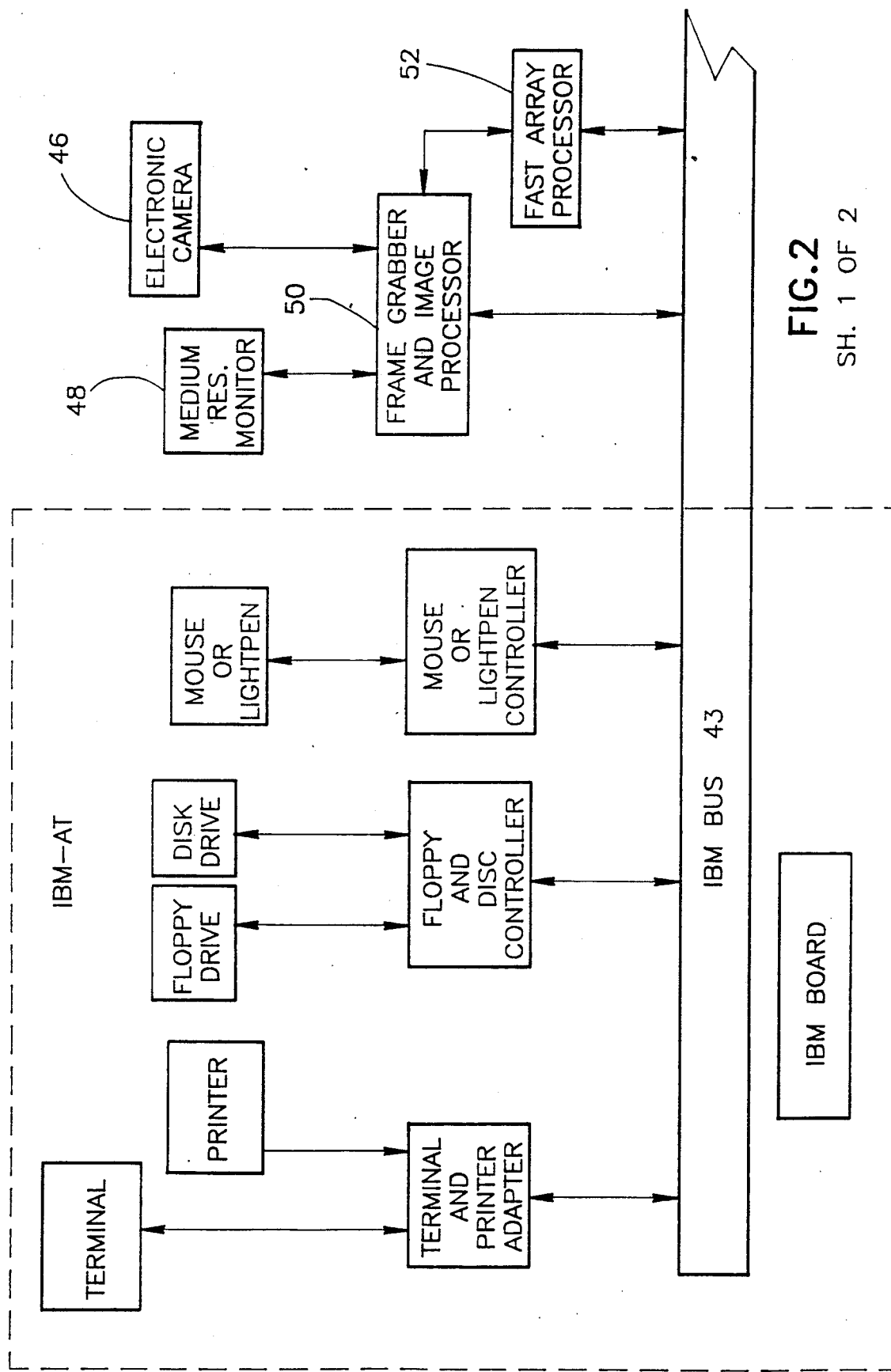
FIGS. 2 and 3 are block diagram illustrations of two possible configurations of a computer controlled laser surgery system constructed in accordance with the preferred embodiments of the invention.

Reference is now made to FIG. 2, which illustrates an embodiment of the computer controlled laser surgery system based upon a personal computer 42, such as an IBM AT, typically comprising a coprocessor, a terminal and printer adapter, a floppy and hard disk adapter, and an input adapter for input elements, such as a mouse, a track ball or a light pen adapter. An accelerator and memory expansion board 44, such as the INBOARD-386 manufactured by Intel, is typically included to improve the performance. The personal computer 42, connected to the appropriate input/output elements, would typically serve as the CCM 22, MMI 24, and the input/output elements CRT 26, light pen 28 and printer 30 in the functional description, and its bus 43, would serve to connect the components described hereinbelow.

In accordance with the present embodiment of the invention, the area of interest is typically imaged by an electronic camera 46, such as the CAM 3000/CCD 3000 from Fairchild, having a 30 frame per sec internal clock timing and serving as the IAU 34. A medium resolution monitor 48, such as the CONRAC 2600 from CONRAC, displays the image to the operator, thus functioning as CRT 40 of the functional description. A frame grabber and image processor 50, such as the MVP-AT from Matrox Electronic Systems of Quebec, Canada, and processes the image received from the camera 46. To increase the processing speed of the image processor 50, and to extend its capabilities in operations such as binary pattern matching and feature extraction, color classification, and distance determination, a fast array processor 52, such as the MVP-NP from Matrox, is typically included. The frame grabber and image processor 50, as well as the fast array processor 52, typically serve as a combination of the IPU 38 and the IAU I/F 36.

The laser unit 16, in the present embodiment, comprises a laser 54, comprising both an Ar high energy surgical laser head 53 and a He-Ne low energy aiming laser head 55, and a general purpose digital input/output module 56. The laser 54 is typically the Ar Laser 920 from Coherent Inc. of Palo Alto, Calif. of the U.S.A., and the input/output module 56 is typically the PCI-20004M from Burr Brown of Tucson, Ariz. of the U.S.A., which serves as the OCU 18 as well as the SLS I/F 32. Module 56 typically controls the general operation of the surgical laser 54, controlling its function and parameters.

In the present embodiment, the BDD 14 comprises five stepper motors 58, such as the MO-103 stepper motor and the ST-143 stepper motor driver from Alpha Products of Darien, Conn. of the U.S.A., and five stepper motor controllers 60, such as the SC-149 also from Alpha Products, to ensure that it is possible to position either of the two laser beams on any point of the area of interest. Each motor 58 creates movement in only one of the x, y, z, pitch or yaw directions. In another embodiment only three motors 58 and three controllers 60 are included; the choice between the two embodiments will depend on the number of degrees of freedom needed to reach all target points in the area of interest.

Figure 3:
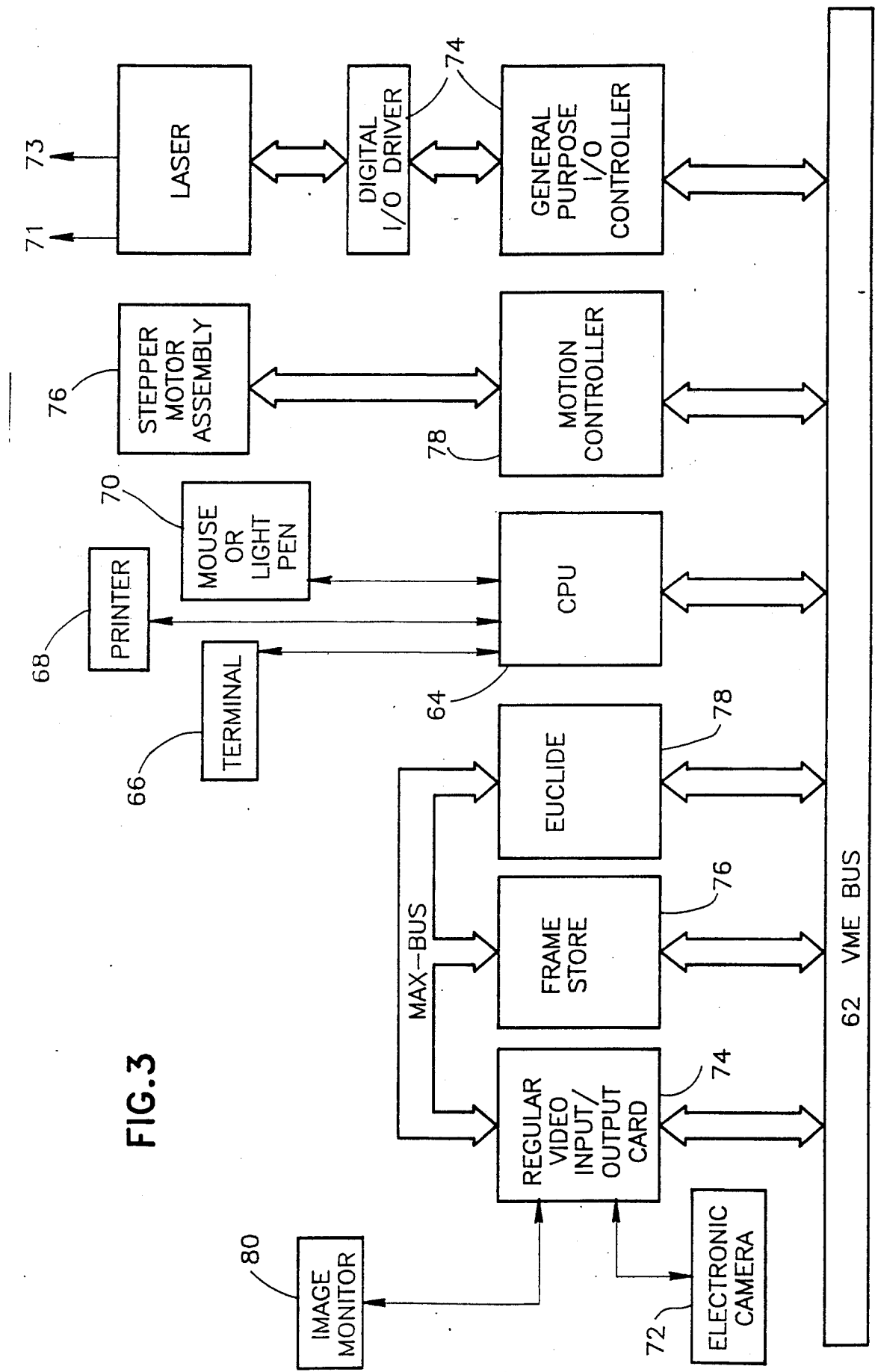

An alternate embodiment of the computer controlled surgical laser system, which performs at a faster rate than that described hereinabove, is illustrated in FIG. 3. It is typically based on a VME bus 62 connected to a CPU (Central Processing Unit) 64, such as the MVME-1334 from Motorola. In this embodiment, a terminal 66, such as the VISUAL 603 from Visual Technology of Tewksbury, Mass. of the U.S.A., a printer 68, such as the EPSON FX-80 from Epson, and an RS232 output mouse or a light pen 70, such as FT-156 with PXL-350 from FTG Data Systems of Stanton, Calif. of the U.S.A., are typically connected to the CPU 64. As in the previous embodiment, the CPU 64 combines the tasks of the CCM 22, the MMI 24, and the input/output elements CRT 26, light pen 28, and printer 30.

In the second embodiment of the invention, the electronic camera 72, performing the tasks of the IAU 34, is typically equivalent to the electronic camera 46.

The image processing tasks of the IPU 38 as well as the interface tasks of the IAU I/F 36, for the second embodiment of the invention, are typically performed by a regular video input/output control card 74, such as the DIGIMAX from Data Cube of Peabody, Mass. of the U.S.A., a frame store board 76, such as FRAME STORE from Data Cube, and a very fast digital signal processor 78, such as EUCLIDE from Data Cube. The digital signal processor 78 typically performs the desired image processing algorithms, while the frame store board 76 stores the image information and performs some data manipulation.

As per the previous embodiment of the invention, the laser unit 16 comprises a laser 72, comprising both an Ar high energy surgical laser head 71 and a He-Ne low energy aiming laser head 73, and a general purpose digital input/output driver 74 which typically serves as the OCU 18 as well as the SLS I/F 32 which controls the function and parameters of the surgical laser. In the present embodiment, the surgical laser 72 will typically be of the same type as that of the previous embodiment of the invention, while the input/output driver 74 will typically be the MPV 940 from Burr Brown with the ACX 946 Digital I/O Driver from Burr Brown mounted to it.

As per the previously described embodiment, the BDD 14 comprises five stepper motors 78, typically of the same type as previously described, and five stepper motor controllers 76, typically of the same type as previously described. As per the previously described embodiment, it is possible for BDD 14 to comprise three stepper motors and three stepper motor controllers.

In the present embodiment, the image monitor 80, performing the tasks of the CRT 40 in FIG. 1, (i.e. displaying the image of the area of interest) is of the same type as in the previous embodiment.

Figure 4:
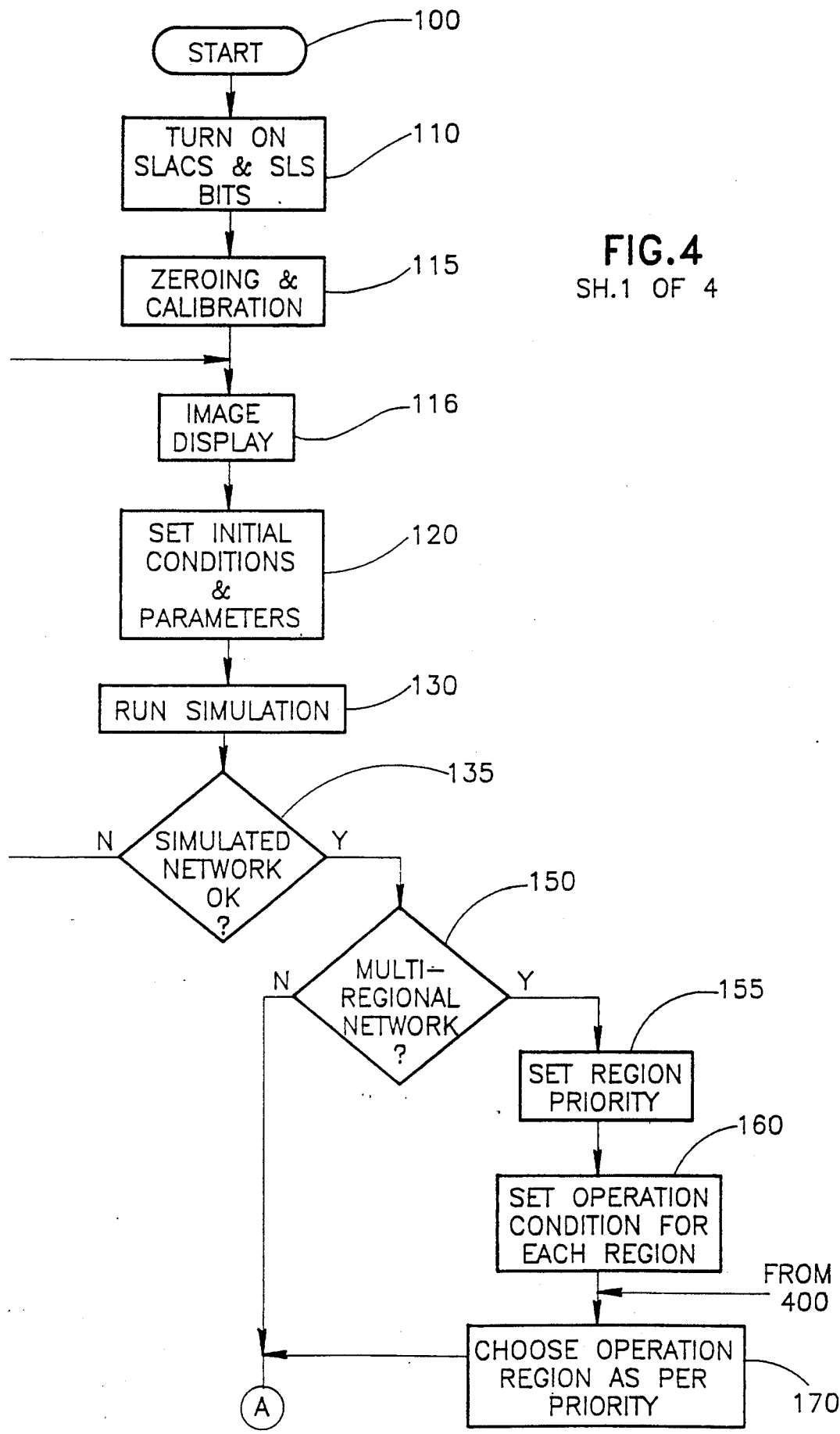
FIG. 4 is a flow chart illustration of an automatic technique for carrying out laser surgery using the apparatus of FIG. 1.
Figure 4:
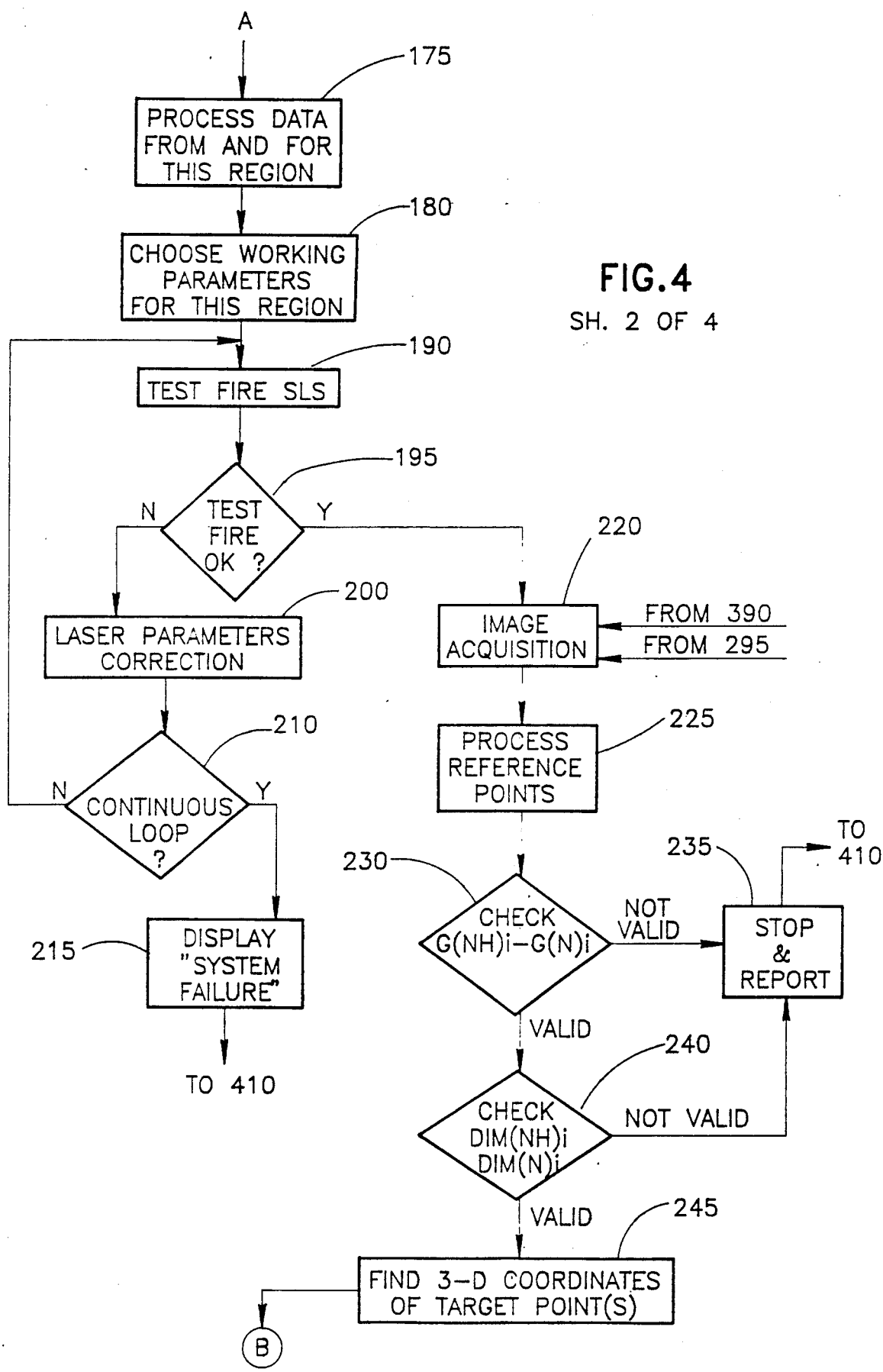
Figure 4:
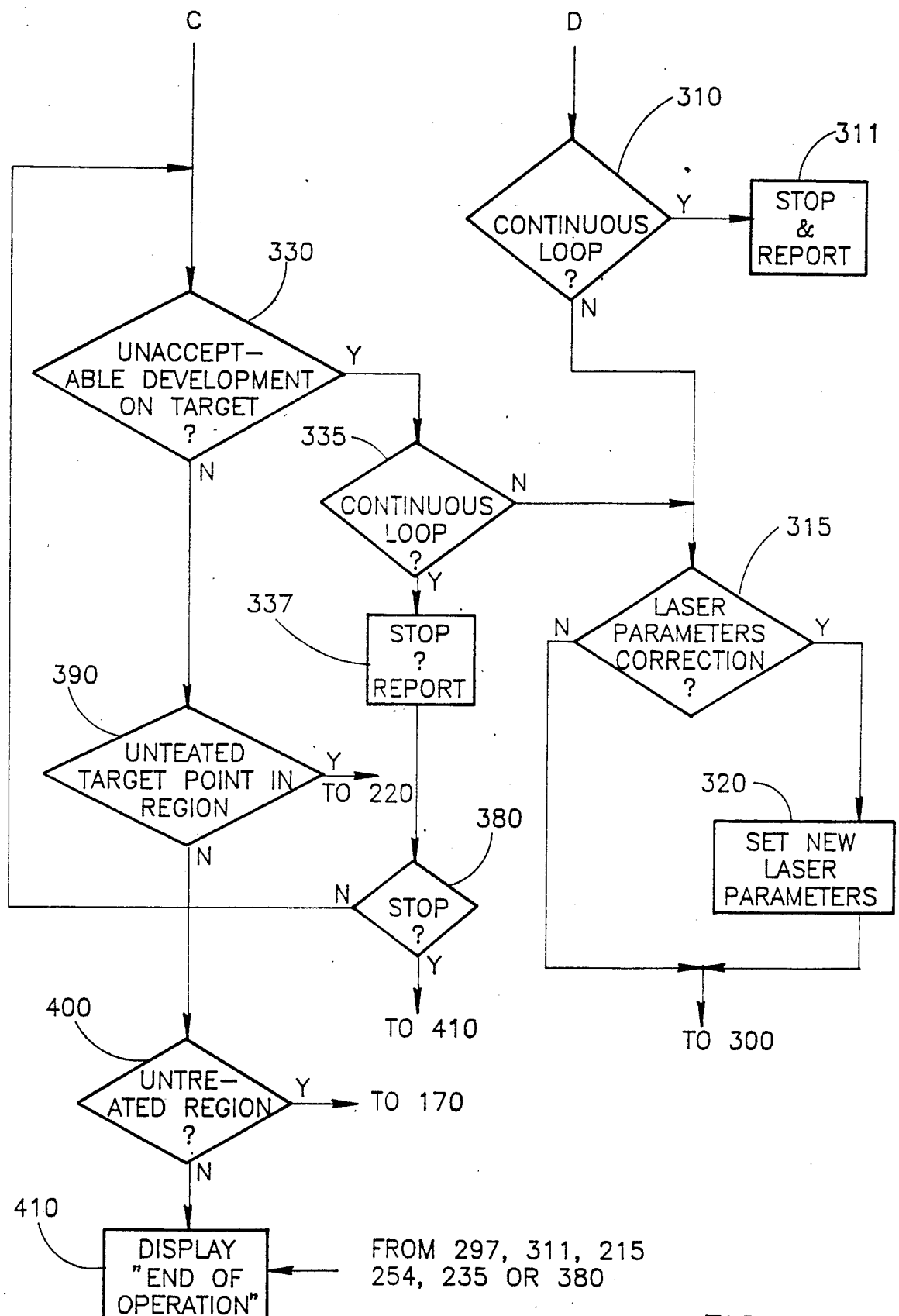

Reference is now made to FIG. 4 which illustrates, in flow-chart form, an automatic mode of operation of the apparatus described hereinabove. The Semi-Automatic alternative mode of operation described hereinabove with respect to FIG. 1 follows the flow chart illustrated in FIG. 4 only for the input and maintenance of beam parameters, as described hereinbelow. The Manual alternative mode of operation described hereinabove with respect to FIG. 1 does not follow the flow chart, nor does the Diagnosis mode of operation.

In the first step, referenced 100, the system is turned on and the operating software is automatically loaded.

In step 110, the system automatically turns on the SLACS 12 and SLS 10 subsystems and performs a BIT (Built In Test), a battery of all the tests necessary to ensure that all components of the system are in proper working order. In the event that this is not the case, the system will display a message to the effect that the test results were negative and then move to step 410 to stop system operation.

If all components are indeed in order, the system proceeds automatically to step 115, in which zeroing and calibration of the instruments component in the system are performed.

In step 116, an image of the area of interest is displayed on one of the monitors of the system, preferably the image monitor, CRT 40. The image displayed is preferably identical to what the operator may see through a viewing unit.

The system then proceeds automatically to step 120. At this stage the operator is asked to set the operation parameters, which preferably include the desired laser beam energy; spot size; minimum distance between burns; operation site limits or burns and critical sites, such as blood vessels, fovea etc. The parameter values set by the operator preferably will be thereafter displayed on one of the monitors, typically CRT 26, of the system.

In addition, the discrete or continuous mode of operation of the laser is chosen. In the discrete mode, typically employed in Pan Retinal Photocoagulation (PRP), there are multiple target points, each representing the location at which a burn will be performed. In the continuous mode, typically employed in Photo Radiation Therapy (PRT), there is only one target point, representing the entire operation region, which the laser beam scans in a generally continuous manner.

After the parameters are set, the operator will be asked to delimit the outermost boundary of the site that will undergo the operation, preferably on the screen of the image monitor where the image of the area of interest is displayed and by means of a light pen or cursor. In the same manner, the operator preferably may delimit sub-regions within the outermost boundary previously delimited, if he so desires. The operator will preferably be allowed to use blood vessels as delimiting lines. Thus a network will be defined on the screen.

The operator will then be asked to set the minimum distance between the burn pattern and the delimiting lines, thus providing safety zones around the delimiting lines.

Finally, the operator will be asked to choose the system mode of automatic, semi-automatic or manual. The system mode can also be changed at any time during system operation by pressing a system mode key on the keyboard of MMI 24 (FIG. 1).

Thus at the completion of step 120, the system mode, laser parameters, operation region and sub-regions, the operation mode and the operation conditions have all preferably been determined, and the system is ready for a simulation run.

In the simulation run, designated step 130, the system will automatically operate low-energy laser head 20a, a laser of sufficiently low power so as to be under the threshold of biological damage. Laser 20a will trace the network, as defined by the operator, in the area of interest. An image of the traced network will then appear, superimposed on the network previously defined by the operator, preferably on the screen of the image monitor, CRT 40. This will enable the operator to verify the correlation between the network traced by the system and the network he himself previously defined.

The simulation run typically comprises the following steps described in detail hereinbelow; defining a region priority system (step 155), choosing a current operating region (step 170), preprocessing an image of the region in order to identify the location of the region boundaries in the image (step 175), selecting the working parameters, as defined in step 120, relating to the current region (step 180), acquiring and preprocessing an image (steps 220–225), identifying the coordinates of a target point in the current image (steps 230–245), aiming the SLS beam at the current target point (step 247–255), and firing on the target point with a low energy laser beam (step 300). The series of steps 225–300 are repeated until the plurality of the target points along the boundaries of the current region have been traced. The series of steps 170–300 are repeated until the boundaries of the plurality of regions have been traced.

In step 135 the operator will be asked whether or not the correlation between the network he defined and the network traced by the system is to his satisfaction. If the answer is negative, the system will return, either automatically or manually, to the stage of step 120 at which the network is defined, in order to redefine its boundaries and/or its subboundaries.

If the operator's answer to the question posed to him in stage 135 is in the affirmative, the system will proceed, either automatically or manually, to step 150 described hereinbelow.

In step 150 the operator is asked whether or not the network previously defined is multi-regional. If the answer is negative, the system proceeds directly to stage 175, described hereinbelow. If the answer is affirmative, the system will first proceed to step 155, described hereinbelow.

Alternatively, the system may automatically determine whether the network is multi-regional or not, and accordingly proceed automatically to step 155, or directly to step 175.

In step 155, the operator will be asked to define the relative priorities of the regions in the multi-regional network, that is, in what order the regions will have to be treated. After the priorities have been determined, the system will automatically proceed.

In step 160, the operator will be asked to define specific operation conditions, or laser parameters, for each region, such as burn size and pulse duration. Alternatively, steps 150 to 160 may be integrated into step 120.

In step 170, the system automatically chooses the first operation region, in accordance with the previously defined priorities. When this step is repeated, at later stages, the system chooses the operation region with the highest priority remaining. The system then automatically proceeds.

In stage 175, the system processes the operation conditions data previously introduced by the operator in addition to the data acquired from the area of interest by the IAU 34 (FIG. 1). The processing of the data from the area of interest involves acquiring the image, preprocessing the image via standard techniques such as signal enhancement, restoration, calibration, and data compression, identifying the boundaries apparent in the image using edge detection techniques such as the Hough transform and identifying the selected region via image matching techniques such as those described by J. K. Aggarwal and W. W. Martin in the article "Dynamic Scene Analysis," pages 40–73 of the book Image Sequence Processing and Dynamic Scene Analysis, edited by T. S. Huang, Springer Verlag, 1983 and incorporated herein by reference. Additionally, the processing includes defining the sequence of burn locations (i.e. sequence of target points) by which the selected region will be burned. Generally, the first target point will be located near some easily identifiable location, such as near the junction of two boundaries defining the selected region or near a reference point where the actual location will depend on the size of the safety zones about the boundaries or reference points, on the allowed spot size and on minimum distance between burns, as defined in step 120. The second target point is located as close to the first target point as allowed by the burn size parameters described hereinabove. The remaining target points are defined according to the method described above. If the surgeon wishes to cauterize an artery in the selected region, he will have defined the exact location of the target point by mouse or light pen in step 120 and the specific location will be included among the target points of the selected region. Alternatively, the surgeon will have previously defined, in step 120, the characteristics of an artery needing cauterization and the system will have calculated which locations in the selected region fit the characteristics. The resulting locations will be included among the target points of the selected region. The number of target points needed to burn the entire region will depend on the size of the region and on the burn size parameters and is calculated in step 175.

It will be appreciated that IAU 34 will continuously feed the system with information from and about the area of interest in general, and the current operation region in particular, at a predetermined rate, typically of 25 frames per second. The CCM 22 (FIG. 1) performs the processing described hereinabove, comparing the acquired image data or the relevant portion of it, at every frame or at pre-determined frames, in accordance with previously introduced instructions, with the data in the preceding frame, and decide upon the next step in accordance with the initial instructions introduced in step 120, as a part of the steps described hereinbelow.

In step 180 the system automatically selects the working parameters pertaining to the operation region being treated from the totality of working parameters previously introduced by the operator.

In step 190 the system will automatically test-fire the SLS subsystem 10. The Ar laser head 20b, or part of it, will be targeted at the sensor unit 21 standardly incorporated into the laser system and will fire a beam at the sensor unit 21. The output from the sensor unit 21 will be analyzed and compared to the laser beam parameters introduced by the operator in step 120. It should be noted that the Ar laser beam is typically not allowed to reach the operation site at this stage.

In accordance with the instructions introduced in step 120, the system will automatically decide, or the operator will manually decide, in step 195, whether the actual beam parameters fit those introduced by the operator in step 120. If the answer is in the affirmative, the system will automatically proceed directly to step 220, described hereinbelow.

If there is a discrepancy unacceptable according to the parameters introduced in step 120, the system will automatically adjust the effective beam parameters in step 200, and return to step 190 in order to perform a repeat test-fire.

A continuous loop test is performed in step 210 to prevent the system running a continuous loop, in the event of repeated failure to correctly adjust the actual beam parameters. The maximum number of attempts allowed to correct the effective beam parameters is set by the operator in step 120. If the system fails the continuous loop test, a message to that effect, typically "SYSTEM FAILURE", will be displayed, preferably on the system monitor, CRT 26. From step 210 the system will automatically proceed to step 410 to stop system operation.

As described hereinabove, if there is no unacceptable discrepancy between the actual beam parameters and those introduced by the operator in step 120, the system will proceed automatically from step 195 to step 220.

In step 220, a new image, $I(n+1)$, is acquired by IAU 34 (FIG. 1) and transmitted to the IPU 38 via the IAU I/F 36. The image, $I(n+1)$, will be processed and the exact location of the current target point will be calculated in the following steps.

In step 225, the system processes the data acquired from the image, $I(n+1)$, acquired in step 220. The processing involves substantially the same operations performed in step 175, such as image enhancement and edge detection, and produces an enhanced image $I_e$ with well defined boundaries. If $I(n+1)$ is not the first image, then burns will also be apparent in the enhanced image $I_e$. In addition to the processing, the system identifies, typically using the techniques described in the previously mentioned "Dynamic Scene Analysis", which boundaries are apparent in the enhanced image $I_e$, the location of the currently defined region and the locations $G(n+1)_i$ of features in the region, known as reference points. It should be noted that subscript i represents the ith reference point and $G(n+1)$ represents the location of a reference point in the n+1th image, $I(n+1)$.

Since, in step 175, the locations of the plurality of target points in the current region were defined, the system checks that the area of interest, as defined by the reference points, has not moved. If it has, the locations of the remaining target points are redefined with respect to $G(n+1)_i$. The logic is as follows.

In step 230, the x-y location of every reference point $G(n+1)_i$ is vectorally substracted from the corresponding location $G(n)_i$ in the previous image, $I(n)$, according to the technique outlined in the article by R. A. Jones and C. D. Bowling, "An Adaptive Gradient Approach to Displacement Estimation," pages 235-248 of the book, Image Sequence Processing and Dynamic Scene Analysis, edited by T. S. Huang. The article is incorporated herein by reference. It should be noted that the x- and y- axes are the vertical and horizontal axes of the image plane of the IAU 34; the z-axis is the axis perpendicular to both the x- and y-axes and is typically the axis along which the IAU 34 moves to approach the patient.

If the displacement calculated in step 230 indicates that the reference points have moved significantly, where significantly indicates greater than a tolerance predetermined in step 120, typically the same order of magnitude of the burn size, and where the movement is typically caused by involuntary or voluntary eye movements or accidental camera movements, then $I(n+1)$ is defined to be displaced from $I(n)$. Otherwise, $I(n+1)$ is denoted as fixed with respect to $I(n)$.

If the displacement calculated in step 230 is greater than a second, larger tolerance, as predetermined by the size of the field of view of the IAU 34 (FIG. 1), then the displacement is too large to be compensated. Thus, the displacement is declared NOT VALID and the system stops and reports the error in step 235.

If the displacement is a valid displacement or if there is no displacement, a check is made that the area of interest has remained in focus. The check is performed, in step 240, by comparing the dimensions of the reference points in the previous image $I(n)$ to their dimensions in the current image $I(n+1)$, where $dim(n+1)_i$, for example, is the number of pixels the ith reference point occupies in the image $I(n+1)$. The actual z-axis locations are typically calculated using standard optical geometry and/or triangulation calculations.

Each dimension $dim(n+1)_i$ is compared to the corresponding dimension $dim(n)_i$ of the previous image $I(n)$, also in step 240, and the displacement is compared to a predetermined tolerance, typically based on the focal length of the IAU 34. If the displacement is larger than the tolerance, indicating that the movement which occurred in the surgical location is too large to be compensated for by refocusing, then the displacement is declared NOT VALID and the system stops and reports the error in step 235.

If neither the x-y displacement nor the z-displacement is larger than the tolerance, then the system proceeds to step 245 and calculates the two-dimensional location of the current target point, and that of any remaining target points if $I(n+1)$ is not fixed with respect to $I(n)$. It will be appreciated that the location of the current target point will depend on its location as defined in step 175, the size of the previous burn whether or not that burn conformed to the operator delimited parameters, and the current locations $G(n+1)$ of the reference points. Thus, the current target point location is calculated by adding the calculated displacement to the location of the current target point in $I(n)$ and adding or subtracting the difference between the operator delimited burn size and the actual burn size.

It will also be appreciated that the target point location calculation described hereinabove is also operative for calculating three-dimensional locations of target points in a three-dimensional object, such as a tumor.

In step 247 the location of the SLS beam (i.e. the beam of either of the two lasers heads 21a and 21b) at which it can point at the current target point is calculated. The transformation from image coordinates to SLS beam coordinates typically depends on the size of the field of view of the IAU 34 and on the magnification of the system.

In step 250, the system automatically checks whether or not the beam of the SLS subsystem 10 is aimed at the target point. If the answer is in the affirmative, the system automatically proceeds directly to step 260. If the answer is negative, the system checks the validity of the requested motion of the laser beam and if it is valid, aims the beam of the SLS subsystem 10 at the target point, in step 255, and only then proceeds to step 260. The validity check is typically included to ensure that any physical constraints on the laser motion are considered before commanding the laser to move. Should the laser be in an extreme position and thus, unable to perform the commanded motion, the system stops and reports this fact in step 254.

In step 260, the surgeon is asked whether he desires a test-firing of the beam to be performed. If he replies negatively, the system proceeds automatically to step 300, described hereinbelow.

If he replies affirmatively, the system proceeds to step 267. A test-firing of the beam of the aiming laser 20a of the SLS subsystem 10, is performed and subsequently, the operator is asked, in step 275, whether the accuracy of the hit is satisfactory or not. If the reply is negative, the system automatically returns to step 220, via step 295 described hereinbelow, in order to try to correct the aiming error. If the reply is positive, the system proceeds to step 300, described hereinbelow.

A continuous loop test is performed in step 295 to prevent the system running a continuous loop, in the event of repeated failure to correctly aim the beam of the SLS subsystem 10. The maximum number of attempts allowed to correct the aiming error is set by the operator in step 120. If the system fails the continuous loop test, a message to that effect, typically "SYSTEM FAILURE", will be displayed, preferably on the system monitor, CRT 26. From step 295 the system will automatically proceed to step 410 to stop system operation.

Alternatively, the decisions in steps 260 and 275 can be made automatically by the system, in accordance with instructions and parameters previously introduced by the operator in step 120.

In step 300, the system automatically fires the surgical laser head 20b of the SLS subsystem 10. After the firing is performed, the system automatically proceeds to step 305.

In step 305, the data regarding the current operation region, acquired by IAU 34 (FIG. 1), is processed by substantially the same techniques of steps 175 and 230 and is compared with the data acquired immediately before the firing, and/or with the instructions and parameters, introduced in step 120, regarding operation conditions. The system then proceeds to a series of steps 309 to 400 in which, based on the previously introduced instructions and parameters, it makes decisions regarding the required course of action.

In step 309 the system decides whether or not the target point requires further treatment. A target point typically requires further treatment if the laser beam did not successfully burn the target point, as can occur if the laser is not focussed properly, or if it incorrectly located the burn on top of a previous burn. If the answer is affirmative, as decided automatically according to the parameters delimited by the operator in step 120, or manually, as decided by the surgeon upon inspection of the burn as shown in the image monitor CRT 40, the system proceeds to a step 310.

A continuous loop test is performed in step 310 to prevent the system running a continuous loop, in the event that the target continuously requires more treatment. The maximum number of attempts allowed to repeat the treatment of the target is set by the operator in step 120. If the system fails the continuous loop test, a message to that effect will be displayed, preferably on the system monitor, CRT 26. From step 310 the system will wait for the surgeon to respond after examining the laser, and upon his response, will automatically proceed to step 315 to continue the surgery.

In step 315, the system decides whether or not the laser beam parameters need to be adjusted for the purposes of the repeat-firing decided upon in step 309. If the answer is affirmative, the system proceeds to step 320, in which the laser beam parameters are re-set. The system then automatically returns to step 300.

If the answer to the question of stage 315 is negative, that is, if the laser beam parameters do not need adjusting prior to the repeat-firing decided upon in step 309, the system automatically returns directly to step 300, and step 320 is circumvented.

If the answer to the question in step 309 is negative, that is, if the target point does not require further treatment, the system automatically proceeds to step 330.

In step 330, the system checks the processed data to ascertain whether any unacceptable developments, such as creating a burn within the safety zone, have occurred in the operation region. An unacceptable development can be defined automatically, from the operation conditions entered in step 120, or it can be defined by the surgeon upon visually inspecting the operation region on image monitor CRT 40. If there are unacceptable developments, the system will return to step 315 in order to attempt to rectify the situation by an additional firing of the laser.

A continuous loop test is performed in step 335 to prevent the system running a continuous loop, in the event of repeated failure to correct the unacceptable developments. The maximum number of attempts the operator wishes the system to attempt to correct the unacceptable developments is set in step 120. If the system fails the continuous loop test, a message to that effect will be displayed, such as "OPERATOR'S INTERVENTION NEEDED", preferably on the system monitor, CRT 26. From step 335 the system will wait for the surgeon to respond after examining and possibly changing, one or more parameters of the entire system or of one of more of the sub-systems thereof, and upon his response, will automatically proceed to step 380 to query the surgeon whether or not he wishes to shut down the system.

If the reply to the query of step 380 is in the affirmative, the system will proceed to step 410, described hereinbelow.

If the reply to the question in step 380 is negative, that is, if the operator does not wish to shut down the system, the system returns to step 330. If no unacceptable developments have occurred in the operation region, the system proceeds to step 390.

In step 390, the system checks whether or not there remain any untreated target points in the operation region. If the answer is in the affirmative, the system automatically returns to step 220 in order to commence treatment of the next target point.

If there are no remaining untreated target points in the operation region, the system proceeds from step 390 to step 400.

In step 400, the system checks whether or not there remain any untreated regions in the network. If the answer is in the affirmative, the system automatically returns to step 170 in order to commence treatment of the next region.

If there are no remaining untreated regions in the network, the system proceeds from step 400 to step 410.

In step 410, the system informs the operator that it has completed its functions, preferably by displaying a message on the system monitor CRT 26 that typically reads "END OF OPERATION".

It will be appreciated by persons skilled in the art that the present invention is not limited by what has been particularly shown and described hereinabove. Rather the scope of the invention is defined only by the claims which follow:

I claim:

1. Apparatus for computerized laser surgery comprising:
   means for acquiring in real time a visually sensible image of the area of surgery;
   laser surgical means for directing a laser beam and being operative in a simulation mode to verify correct aiming and to produce a visible indication of laser impingement on the area of surgery and operative in a surgical mode;
   display means for displaying said visually sensible image and said visible indication in overlay over said visually sensible image; and
   automated means for operating said laser surgical means in said surgical mode of said simulation.

2. Apparatus according to claim 1 in which said means for acquiring an image are electro-magnetic means.

3. Apparatus according to claim 1 in which said means for acquiring an image incorporate computerized tomography.

4. Apparatus according to claim 1 in which said means for acquiring an image incorporate catheter-based imaging systems.

5. Apparatus according to claim 1 and wherein said laser surgical means comprises at least two laser heads including a low energy laser head and a high energy surgical laser head.

6. Apparatus according to claim 5 and wherein said low energy laser head transmits, during operation in said simulation mode, a laser beam over substantially the same optical path to be subsequently traveled by laser energy from said high energy laser head in said surgical mode.

7. Apparatus according to claim 5 in which said laser surgical means transmits, at a plurality of individual laser beam impingement locations, first low energy laser energy and subsequently, high energy laser energy.

8. Apparatus according to claim 1 in which said laser surgical means transmits only high energy laser energy.

9. Apparatus according to claim 1 in which said automated means comprises means for monitoring the results of surgical procedures already carried out.

10. Apparatus according to claim 9 in which said automated means also comprises means for determining whether the results of surgical procedures already carried out have predetermined optical characteristics.

11. Method for computerized surgery including the steps of:
    tuning parameters of a beam of a surgical laser; aiming said surgical laser at a plurality of surgery points in an area of surgery;
    low energy firing of a low energy laser beam at an operator indicated surgery point;
    displaying in real time a visually sensible image of the area of surgery and a visible indication of the impingement of said low energy laser beam in overlay over said visually sensible image, thereby to ensure that said surgical laser is correctly aimed; and
    high energy firing of said surgical laser at said operator indicated surgery point thereby to treat said point.

12. A method according to claim 11 and which also includes the step of determining whether the results of surgical procedures already carried out have predetermined optical characteristics.

13. A method according to claim 11 and wherein said step of aiming is performed manually.

14. A method according to claim 11 and wherein said step of aiming is performed automatically.

15. A method according to claim 11 and wherein said step of tuning is performed automatically.

16. Method for computerized surgery including the steps of:
    simulating the results of operator indicated laser surgical procedures on an area of surgery by displaying in real time a visually sensible image of the area of surgery and displaying, in overlay over said visually sensible image, a visible indication of the impingement of a low energy laser beam which is aimed by an operator onto a desired operator indicated surgery point in the area of surgery;
    tuning parameters of a beam of a surgical laser; aiming said surgical laser at each point of the surgery; and
    high energy firing of said surgical laser at said operator indicated surgery point thereby to treat said point.

17. A method according to claim 16 and wherein said step of aiming is performed manually.

18. A method according to claim 16 and wherein said step of tuning is performed manually.

19. A method according to claim 16 and wherein said step of tuning is performed automatically.

* * * * *

UNITED STATES PATENT AND TRADEMARK OFFICE
CERTIFICATE OF CORRECTION

PATENT NO. : 5,049,147

DATED : September 17, 1991

INVENTOR(S) : Nissim N. Danon

It is certified that error appears in the above-identified patent and that said Letters Patent is hereby corrected as shown below:

Column 15, line 28:
In claim 1, last line, please delete the words "of said simulation"

Signed and Sealed this

Nineteenth Day of October, 1993

*Attest:*

BRUCE LEHMAN

*Attesting Officer*       *Commissioner of Patents and Trademarks*